United States Patent [19]

Ernsberger

[11] Patent Number: 5,573,384
[45] Date of Patent: Nov. 12, 1996

[54] PUMP FOR CONVEYING PASTE-LIKE FLOWABLE MATERIALS

[75] Inventor: Klaus Ernsberger, Friedrichshafen, Germany

[73] Assignee: Kaltenbach & Voigt GmbH & Co., Biberach, Germany

[21] Appl. No.: 428,047

[22] Filed: Apr. 25, 1995

[51] Int. Cl.⁶ .................................................. F04B 43/00
[52] U.S. Cl. .......................................... 417/392; 417/474
[58] Field of Search ................................. 417/474, 472, 417/473, 395, 392, 429, 53

[56] References Cited

U.S. PATENT DOCUMENTS

| 2,291,912 | 8/1942 | Meyers | 417/474 |
| 2,821,930 | 2/1958 | Smith | 417/395 |
| 2,926,614 | 3/1960 | Rose | 417/900 |
| 3,305,097 | 2/1967 | Natelson | 417/474 |
| 3,560,114 | 2/1971 | Boyle | 417/474 |
| 3,701,618 | 10/1972 | Wall et al. | 417/474 |
| 4,311,441 | 1/1982 | Scragg et al. | 417/474 |

FOREIGN PATENT DOCUMENTS

| 2640698 | 6/1990 | France | 417/474 |
| 1937161 | 3/1970 | Germany . | |
| 9211393.1 | 2/1993 | Germany . | |
| 2016233 | 7/1994 | Russian Federation | 417/474 |
| 1523718 | 11/1989 | U.S.S.R. | 417/474 |
| 2065789 | 7/1981 | United Kingdom . | |

*Primary Examiner*—Timothy Thorpe
*Assistant Examiner*—Peter G. Korytnyk
*Attorney, Agent, or Firm*—Scully, Scott, Murphy & Presser

[57] ABSTRACT

A pump for conveying flowable paste-like materials, including a conveyer line which has a plurality of conveyer elements sequentially arranged in the longitudinal direction of the conveyer line to selectively displace and release at least a part of the volume of material conveyed by the conveyer line. The pump possesses a working chamber consisting of an annular chamber externally bounded by a housing of the pump and interiorly by a cylinder. The conveyer elements incorporate bellows elements each in the form of a ring of an elastically extensible material acted upon by a pressure medium at a side opposite the material being conveyed, with the bellows elements being formed by a common hose-like bellows which is retained on an inner wall of the housing. A support ring is located between respectively each of the bellows elements for retaining the bellows on the inner wall, with pressure lines located between the support rings and passing through the housing to open into the annular chamber. A control device causes a pressure source and a vacuum source to be alternatively connectable with the pressure lines, with the housing being closed by two end walls in each of which there is selectively provided at least one of an input and output opening.

5 Claims, 2 Drawing Sheets

| | | | | | | | | | | | |
|---|---|---|---|---|---|---|---|---|---|---|---|
| 7a,24a | ● | | | ● | ● | | | ● | ● | | | ● |
| 7b,24b | ● | ● | | | ● | ● | | | ● | ● | | |
| 7c,24c | | ● | ● | ● | | ● | ● | ● | | ● | ● | ● |

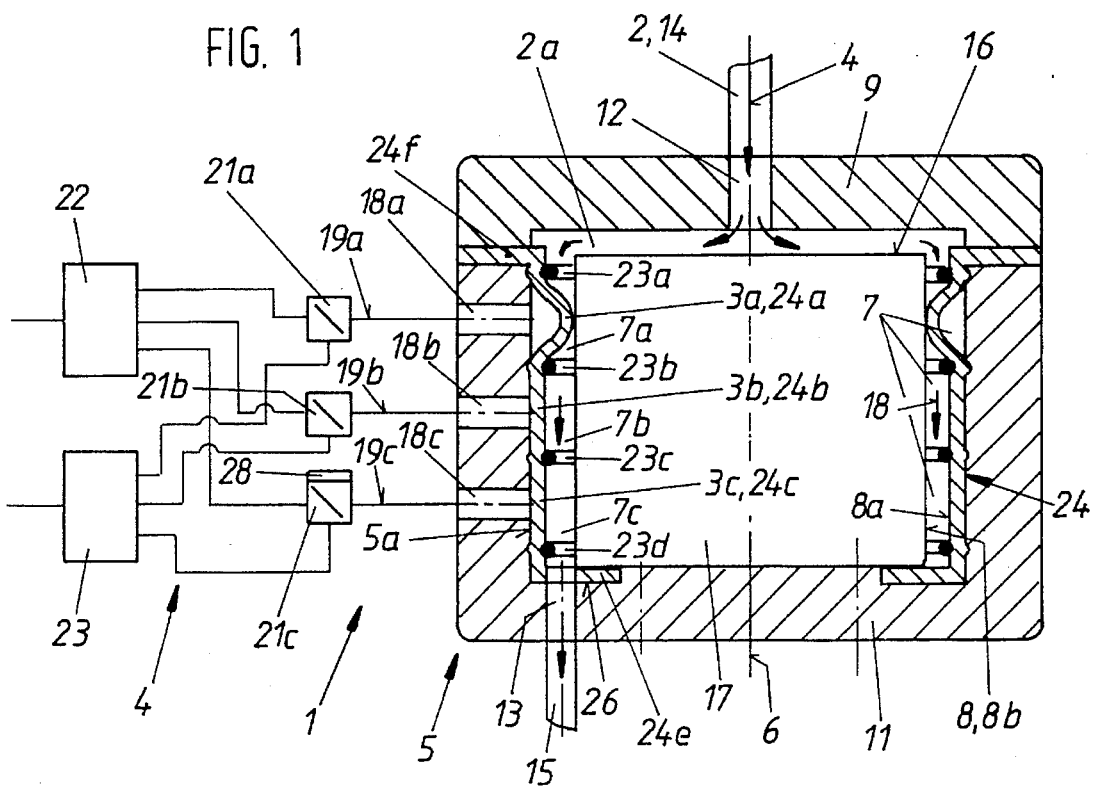

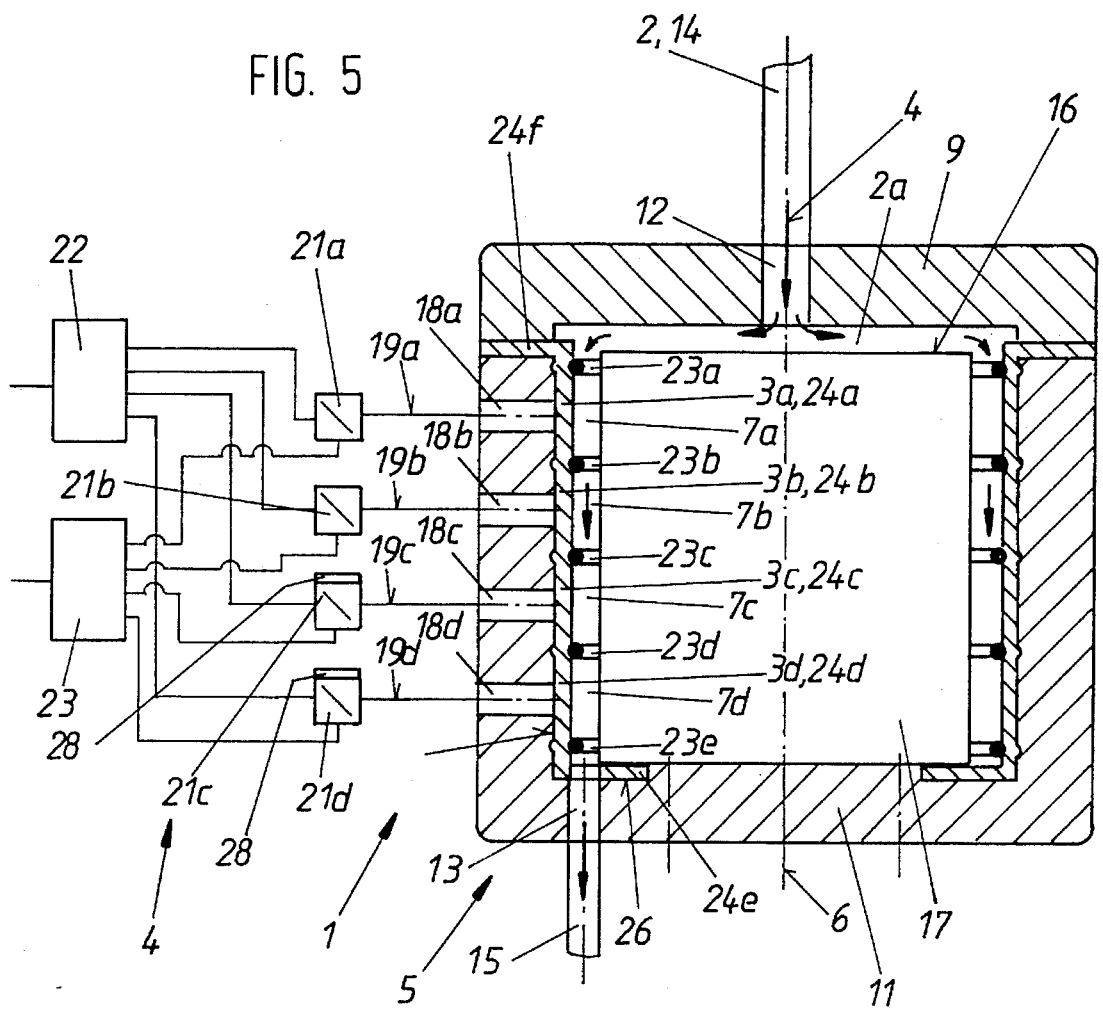

PUMP FOR CONVEYING PASTE-LIKE FLOWABLE MATERIALS

BACKGROUND OF THE INVENTION

1. Field of the Invention

The invention relates to a pump for conveying flowable, in particular paste-like materials, such as for example mud or sludge, oil and chemical industry materials or materials which harden or set such as for example cement mix or plaster of Paris mix, concrete or the like.

2. Discussion of the Prior Art

For conveying flowable, in particular paste-like materials, there are known in the art screw or worm conveyers, hose pumps and so-called impeller pumps. These pumps are disadvantageous for several reasons. On the one hand, they are subject to wear and tear and not only at higher conveying pressures, for example 3 bar or more, but also because of wear and tear caused by the material itself and by contamination of the material. On the other hand, lump or clump-like contamination in the material to be conveyed can damage the pump elements, block the pump and disable the pump. A further disadvantage is found in that the known pumps have a relatively large pump filling volume, which leads to large volume losses in particular when pumping materials which harden or set.

SUMMARY OF THE INVENTION

The object of the invention is to provide a pump for conveying flowable, in particular paste-like materials, which is of simple and compact construction and has a small pump volume.

This object is achieved by the features of claim 1.

In the pump in accordance with the invention, a conveyer line is bounded by a plurality of conveyer elements which are arranged one after the other in the longitudinal direction of the conveyer line, which are moveable transversely of the conveyer line and thereby each displace or release at least a part of the conveyer line volume.

It may thereby be of advantage to associate check valves with the conveyer line, before and/or after the conveyer elements with regard to the conveying direction, which valves allow the passage of material in the conveying direction and block the passage of the material in the opposite direction. By these means there is achieved a loss-free working procedure of the pump and its performance is thereby improved.

In another advantageous configuration, the working chamber of the pump has an annular chamber which is bounded outwardly by a housing of a pump and inwardly by a core, the conveyer elements being formed by means of bellows elements each in the form of a ring of elastically extensible material, which bellows elements can be acted upon—on their side away from the material to be conveyed —by means of a pneumatic or hydraulic pressure medium.

Thereby, the bellows elements may be formed by means of a common bellows of a hose-form, which is divided into bellows sections by means of support rings and which is arranged on the inner wall of the housing, there being provided between the bellows sections respective support rings for retention on the inner walls. Between the support rings, pressures lines are provided which penetrate the housing and open into the annular chamber. The housing is closed by means of two end walls in each of which one or more inlet and outlet openings are arranged, which are connected with the annular chamber.

It is of further advantage to so arrange, configure and/or control the conveyer elements that in their end positions they fully block or fully release or open the conveyer line in each case.

The invention relates also to an advantageous working method for operating a pump, with which method high performance is achieved, whereby the conveyer passage is closed in each timing phase and thus a pressure equalization between the intake side and the delivery side is prevented in pressure pumps. The invention is however also advantageous for conveyer pumps in which conveying alone takes place, without build-up of pressure.

The invention further discloses features which contribute to the solution of problems, improve configuration and function, further extend working life and moreover ensure simple and economical manufacture in particular with regard to mass production.

BRIEF DESCRIPTION OF THE DRAWINGS

The invention and further advantages which can be achieved thereby will be described below with reference to preferred embodiments and simplified drawings, which show:

FIG. 1 a pump according to the invention, in axial section;

FIGS. 2 to 4 in each case a schematic of function of a pump in accordance with the invention having three conveyer elements, FIG. 2 for forwards conveying, FIG. 3 for rearwards conveying and FIG. 4 for rinsing or flushing;

FIG. 5 a pump in accordance with the invention in a modified embodiment;

FIG. 6 a schematic of function for the pump according to FIG. 5, for forwards conveying functional operation.

DETAILED DESCRIPTION OF PREFERRED EMBODIMENTS

The main parts of the pump—generally designated 1—are a conveyer line 2, a plurality of conveyer elements 3a, 3b, 3c which bound the conveyer line 2, which are moveable to and fro transversely of the longitudinal direction of the conveyer line 2 and thereby displace or release a part of the conveyer line volume, and a control device 4 for controlling the movements of the conveyer elements 3a to 3c.

In detail, the pump 1 has a hollow cylindrical pump housing 5 on the inner circumferential wall of which the conveyer elements 3a to 3c are arranged and are moveable preferably at right angles to the longitudinal middle axis 6 of the pump housing 5 inwardly into the working chamber of the pump housing 5 and then again outwardly.

In the present embodiment, the working chamber 7 is an annular chamber, preferably arranged concentrically to the longitudinal middle axis 6, the annular chamber being bounded inwardly by means of a cylindrical wall 8 which is fixed in the pump housing 5 so that the conveyer elements 3a to 3c can work against the wall. For this purpose there may serve pins and/or screws which penetrate a cover or a base of the pump housing 5 in suitable holes and which are schematically indicated in FIGS. 1 and 5 by chain lines 10.

In the present embodiment, the pump housing 5 is formed as a closed housing by means of an inlet end wall 9 and an outlet end wall 11, an inlet opening 12 being arranged preferably centrally in the end wall 9 and an outlet opening 13 being arranged in the end wall 11. A supply line 14 for the medium to be conveyed is connected to the inlet opening 12. A discharge line 15 can be connected to the outlet opening 13, which discharge line is arranged in straight extension of the annular working chamber 7 in the illustrated embodiment. Between the end wall 9 and the end surface 16 of a hollow or solid cylinder 17 providing the cylindrical wall 8—the end surface being opposite to the end wall—a spacing is present which forms a further radial conveyer line section 2a between the inlet opening 12 and the working chamber 7. For attachment of the end wall 9 or 11 to the housing 5, or for attachment of cylinder 17 to the end wall 11, screws may be provided.

The annular working chamber 7 has three working compartments 7a, 7b, 7c lying one after another in the passage direction 18 of the pump 1, which working compartments are bounded outwardly by respective associated conveyer elements 3a to 3c and inwardly by the cylindrical wall 8. Preferably, the conveyer elements 3a to 3c are formed each by a bellows of elastically extensible material such as rubber or plastics, which can be inflated against the cylindrical wall 8 pneumatically or hydraulically and can then move back again. In the present embodiment both movements are effected actively, in that the one or more bellows can be selectively acted upon with over-pressure or vacuum or partial vacuum with respect to the pressure at the intake side of the conveyed medium. This may also be normal pressure, when the intake side already has a pressure above normal pressure as a consequence of a particular filling height. For this purpose there serves in each case a channel 18a, 18b, 18c in the pump housing 5 to which a hose or pipeline 19a, 19b, 19c is connected—each hose or pipeline being connectable by means of a valve 21a, 21b, 21c to a distributor 22 or 23, of which the distributor 22 is connected to a vacuum or partial vacuum source and the distributor 23 is connected to a pressure source.

In the present embodiment, there is provided a common bellows 24—in the form of a hose—for all three above-described bellows, which common bellows is held or biased against the cylindrical inner wall 5a of the pump housing 5 by means of four support rings 23a, 23b, 23c, 23d. For improving retention, annular grooves—preferably rounded in cross-section—may be provided in the cylindrical inner wall 5a at the levels of the support rings 23a to 23c, into which grooves the common bellows is pressed. By means of the support rings 23a to 23c there are formed three bellows elements 24a to 24c which can be selectively acted upon by pressure or vacuum or partial vacuum.

For further improvement of the retention of the common bellows this extends not only up to the end walls 9, 11 but extends in one piece with a radial flange 24f between the pump housing 5 and the end wall 9, and there is further arranged on the end wall 11 an internal flange 24e which can be arranged sunk into a recess 26 of the end wall 11. By these means the common bellows is afforded an additional form-fitting retention, which stabilizes its positioning in addition to the support rings 23a to 23c.

Below, the functioning of the pump 1 will be described with reference to preferred working methods. As shown in FIG. 2, there are represented three functional cycles 1, 2 and 3, lying horizontally one after the other, each having timing phases A, B, C and D, the cycles and timing phases being similar one to another and thus cycle repetitions.

In the schematic representation, the rectangular boxes each signify a working compartment 7a, 7b, 7c of the associated bellows elements 24a, 24b, 24c.

Starting from the final timing phase D of one cycle the bellows element 24b is moved forwards (as shown in FIG. 1) and at the same time the bellows element 24c is moved backwards, to bring about the timing phase A, whereby the volume from the working compartment 7b enters the working compartment 7c but no delivery takes place because the working compartment 7c is being filled.

To bring about the timing phase B, the bellows element 24c is moved forwards, whereby a compartment volume, namely the volume of the compartment 7c, is delivered. Preferably at the same time, the bellows element 24a is moved backwards, whereby a volume corresponding to the working compartment 7a is taken in.

To bring about the timing phase C, the bellows element 24b is moved backwards, whereby a corresponding further compartment volume is taken in and the bellows element 24c remains moved forwards and thus blocks the passage.

To bring about the timing phase D, the first bellows element 24a is moved forwards, whereby likewise no delivery takes place since the last bellows element 24c remains moved forwards.

The bringing about of the next timing phase A has already been described above.

The pressurization and relief or release of the bellows elements 24a to 24c occurs in each case by means of the associated controllable two-way valve 21a to 21c for each bellows element, whereby the two-way valve controls in each case the two states of activation, namely:

the pressurized state of the bellows element, in that the valve 21 delivers a pressure medium (compressed air, pressure oil)—over a supply path which is as short as possible—to the associated bellows element 24a to 24c via the associated distributor 23, the associated relief line to the distributor 22 being closed, and the relief state, in that the valve 21 relieves the pressure effective on the associated bellows element by way of the distributor 22, whereby the bellows element is automatically moved back because of its elasticity, or is connected with the low pressure or partial vacuum side whereby the bellows element is actively moved back. The associated pressure line between the valve 21 and the distributor 23 is closed.

As can be clearly understood from FIG. 3, a rearwards conveying is achieved by a reversal of function, i.e. the bellows elements 24a to 24c are activated in reverse manner, which is made clear by the recognizably mirror-image activation of the bellows elements 24a to 24c in FIG. 3.

For a rinsing or flushing process, the pump 1 may be controlled in the same manner as for the above-described forwards conveying and rearwards conveying, a fluid rinsing or flushing medium being supplied into the pump 1 and correspondingly delivered.

FIG. 4 shows a modification of a rinsing or flushing procedure. As shown by cycle 1, the timing phases A and D correspond to the timing phases A and D for forward conveying according to FIG. 2. In contrast, the rinsing or flushing timing phases B and C differ in that for bringing about the timing phase B the bellows element 24b is moved backwards and the bellows element 24c moved forwards at the same time, and to bring about the timing phase C the bellows element 24b is moved forwards and at the same time the bellows element 24c is moved backwards. To bring about the timing phase D, the bellows element 24b is, on the other hand, moved backwards and simultaneously the bellows element 24c moved forwards. Thereby, the bellows element 24a remains always forwardly moved, that is, closed.

At the next cycle (see cycle 2) the control of the bellows elements is effected in a mirror-image arrangement, so that the bellows element 24c remains always closed and the other two bellows elements are alternately forwardly and backwardly moved.

The control in cycle 3 corresponds to the control in cycle 1.

With the above-described rinsing or flushing procedure, no delivery of the rinsing or flushing medium is effected; there is merely effected a cleaning of the chamber walls by means of an active movement of the bellows elements as described above.

With an arrangement of four bellows elements in accordance with FIG. 5, two bellows volumes can be delivered per cycle—see timing phases B and C. This pump 1 differs in that the following further parts are provided, namely, a bellows element 24d, a channel 18d, a hose or pipeline 19d, a valve 21d and two further lines connecting the valve 21d with the respectively associated distributors 22, 23.

Starting from the timing phase D, in which the bellows elements 24a and 24d are moved forwards, for bringing about the timing phase A the bellows element 24b is closed and at the same time the bellows element 24d is opened, whereby no delivery, but merely a balancing of bellows volumes occurs.

To bring about the timing phase B, the bellows element 24a is moved backwards and at the same time the bellows element 24c is moved forwards, whereby one bellows volume is delivered and at the same time one bellows volume is taken in.

To bring about the timing phase C, the bellows element 24b is moved backwards and at the same time the bellows element 24d is moved forwards, whereby a further bellows volume is delivered and at the same time a bellows volume is taken in.

To bring about the timing phase D, the bellows element 24c is then moved backwards and the bellows element 24a moved forwards, whereby a balancing of bellows volumes takes place.

As the activation schematics illustrate, the delivery and the intake sides of the pump 1 are always separated by at least one forwardly moved bellows element 24a to 24d, so that in no phase can a pressure equalization of the medium to be conveyed take place between the delivery and intake sides. The bellows elements have, thus, not only a conveying function but also a check valve function.

The delivery pressure of the pump 1 is always below the working pressure of the bellows pressurization. However, in contrast to all other kinds of pumps, the delivery pressure can be increased as desired by means of the working pressure, insofar as the strength and stability of shape of the bellows 24 or the bellows elements 24a to 24d allow this to take place, since the sealing effect increases with the working pressure.

The pump 1 according to the invention also allows a dosing of the medium to be conveyed, or a monitoring of the conveyed quantity, by counting the bellows pressurizations. The dose quantity or delivered quantity of one ejection (bellows conveyance volume) is, particularly with low viscosity fluids, very well reproducible so that the dose quantity can be derived for lower pump frequencies by counting the bellows pressurizations. With higher viscosities and higher pump frequencies the dose quantity or conveyed quantity per bellows pressurization reduces, so that a frequency dependent calibration is of advantage. For dosing there is to be associated with the control device—generally indicated by 4—a corresponding dosing device for example having a counter device 28 for the bellows elements which effect delivery (bellows element 24c in the embodiment according to FIG. 2 and bellows elements 24c and 24d in the embodiment according to FIG. 5). The counting device may be associated for example with the associated valve 21c (FIG. 2) or 21c, 21d (FIG. 5) or the line or lines 18c or 19c, or 18c, 19c and 18d, 19d.

Within the scope of the invention it is possible to do without the timing phase D when, in the exemplary embodiment according to FIG. 1, for initiating the timing phase C the bellows element 24a is in each case moved forwards at the same time.

The housing 5, the end walls 9, 11 and the support rings 23a to 23d may be of plastics or metal, in particular corrosion resistant.

I claim:

1. A pump (1) for conveying flowable paste-like materials, including a conveyor line (2) comprising a plurality of conveyor elements (3a to 3d) sequentially arranged in the longitudinal direction of the conveyor line (2) and being movable transversely of the conveyor line selectively displace and release at least a part of the volume of material conveyed by said conveyor line, said pump having a working chamber (7) consisting of an annular chamber externally bounded by a housing (5) of the pump (1) and interiorly by a cylinder (17), the conveyor elements (3a to 3d) comprising bellows elements (24a to 24d) each in the form of a ring of an elastically extensible material acted upon by a pressure medium at a side opposite the material being conveyed, said bellows elements being formed by a common hose-like bellows (24) which is retained on an inner wall (5a) of the housing (5), a support ring (23a to 23d) being located between respectively each of the bellows elements (24a to 24d) for retaining the bellows (24) on said inner wall (5a), pressure lines (18a to 18d) located between said support rings (23a to 23d) and passing through the housing (5) to open into said annular chamber, a control means (4) for causing a pressure source (22) and a vacuum source (21) to be alternatively connectable with the pressure lines, the housing (5) being closed by two end walls (9, 11) in each of which there is selectively provided at least one of an input and output opening (12, 13).

2. A pump according to claim 1, wherein the housing (5) of which at least one of said end walls is integrally formed and the other end walls is detachably attached to the housing.

3. A pump according to claim 2, wherein the inlet end wall (9) has a central inlet opening (12) and a radial conveyer line communicating with the working chamber (7).

4. A pump according to claim 1, wherein the wall (5a) against which the bellows (24) bears in a neutral position thereof includes rounded annular grooves in the plane of the support rings.

5. A pump according to claim 1, wherein the bellows (24) has at least at one free edge thereof, a respectively inner and outer flange (24f, 24e) through which the bellows is form-fittingly arranged and tensioned in a recess (26) and between the housing (5) and an associated end wall (9, 11).

* * * * *

UNITED STATES PATENT AND TRADEMARK OFFICE
CERTIFICATE OF CORRECTION

PATENT NO. : 5,573,384
DATED : November 12, 1996
INVENTOR(S) : Klaus Ernsberger

It is certified that error appears in the above-indentified patent and that said Letters Patent is hereby corrected as shown below:

```
     On the Title Page, after Section "[22]..."
insert the following:

--[30]  Foreign Application Priority Data
           April 28, 1994 [DE]  Germany.......P 44 14 934--
```

Signed and Sealed this

Twenty-first Day of October 1997

Attest:

Attesting Officer

BRUCE LEHMAN
Commissioner of Patents and Trademarks